United States Patent [19]
Urashima et al.

[11] Patent Number: 5,605,992
[45] Date of Patent: Feb. 25, 1997

[54] EMULSION POLYMERIZATION INHIBITOR AND SUSPENSION POLYMERIZATION METHOD USING THE AGENT

[75] Inventors: Nobuaki Urashima, Nara; Hayato Ikeda, Osaka; Mitsuo Kushino, Hyogo; Yoshikuni Mori, Osaka, all of Japan

[73] Assignee: Nippon Shokubai Co., Ltd., Osaka, Japan

[21] Appl. No.: 453,248

[22] Filed: May 30, 1995

[30] Foreign Application Priority Data

May 27, 1994 [JP] Japan .................................. 6-115124

[51] Int. Cl.$^6$ ...................................................... C08F 2/00
[52] U.S. Cl. ........................ 526/217; 562/62; 526/219.5; 526/329.2
[58] Field of Search ................................ 526/217; 562/62

[56] References Cited

U.S. PATENT DOCUMENTS 5,302,681  4/1994  McClain .................................. 526/217

FOREIGN PATENT DOCUMENTS

| | | |
|---|---|---|
| 52-102391 | 8/1977 | Japan . |
| 55-82125 | 6/1980 | Japan . |
| 60-8302 | 1/1985 | Japan . |
| 62-205108 | 9/1987 | Japan . |
| 2284905 | 11/1990 | Japan . |
| 3237105 | 10/1991 | Japan . |
| 561253 | 3/1993 | Japan . |
| 593005 | 5/1993 | Japan . |

OTHER PUBLICATIONS

Computer generated prior art cover page and pp. 1–5; Aug. 2, 1996.

Primary Examiner—Joseph L. Schofer
Assistant Examiner—N. Sarofim
Attorney, Agent, or Firm—Omri M. Behr, Esq.

[57] ABSTRACT

A suspension polymerization of a polymerizable monomer in the presence of an emulsion polymerization inhibitor is disclosed. The inhibitor is an aromatic series compound having a $NO_2$ group, a $SO_3Na$ group, and a secondary amino group, representatively, the following compound. In this suspension polymerization, the production of by-produced microfine particles caused by the emulsion polymerization as the secondary polymerization scheme is repressed.

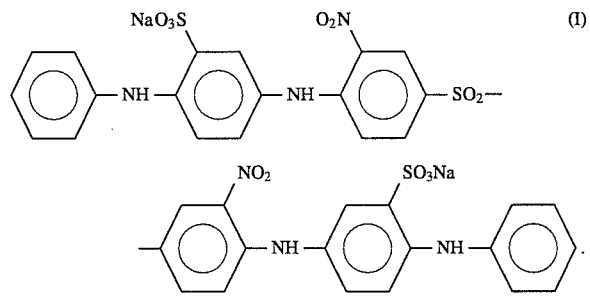

4 Claims, No Drawings

EMULSION POLYMERIZATION INHIBITOR AND SUSPENSION POLYMERIZATION METHOD USING THE AGENT

BACKGROUND OF THE INVENTION

1. Field of the Invention

This invention relates to an emulsion polymerization inhibitor and a suspension polymerization method using the inhibitor. Further, this invention relates to resinous particles obtained by the suspension polymerization and uses therefor. More particularly, this invention relates to a technique in the suspension polymerization for producing resinous particles with a narrow particle size distribution and without heavy metal contamination.

2. Prior Art

Heretofore, as methods for the production of resinous particles, those resorting to mechanical pulverization, to suspension polymerization, and to emulsion polymerization have been known to the art. Of these methods, that which resorts to mechanical pulverization necessitates a huge energy input to pulverize the particles and require many classification steps to enable the resinous particles to be produced with a uniform diameter. Since the minute particles which are obtained by this method are amorphous morphologically, they have room for further improvement in flowability and proofness against flocculation. Although the method which resorts to emulsion polymerization is capable of producing minute particles of uniform diameter, the produced minute particles have a diameter of about 0.1 μm and, therefore, cannot be directly put to such applications as mentioned above. In contrast thereto, the method which resorts to suspension polymerization allows relatively easy production of resinous particles of a desired diameter because it comprises preparing suspended particles of a monomer by mechanical stirring and subjecting the suspended monomer particles to polymerization. It further enjoys such advantages as obviating the necessity for using a solvent and facilitating the reaction control.

It has been known, however, that the suspension polymerization entails secondary formation in the aqueous phase of minute particles due to emulsion polymerization. The secondary reaction lowers the yield of the main polymerization and degrades the stability of this polymerization. Further, since the minute particles formed as described above by emulsion polymerization adhere predominantly to the phase boundary of the particles produced by suspension polymerization and cannot easily be completely removed therefrom, they suffer impairment of the physical properties of the produced resinous particles. Particularly when the resinous particles to be obtained by suspension polymerization are required to have such a small diameter as to be in the approximate range of 0.1 to 500 μm, for example, and since the amount of a dispersion stabilizer to be added to the aqueous phase for ensuring stabilization of the minute suspended particles is large as compared with that for ordinary suspension polymerization, the amount of the polymerizable monomer dissolved in the aqueous phase at the step of dispersion and the step of polymerization is increased possibly to the extent of causing the problem of by-production of minute particles due to emulsion polymerization.

As a means for preventing the suspension polymerization from causing emulsion polymerization in the aqueous phase, the addition of an inorganic water-soluble inhibitor to the system has been known to the art. For example, JP-A-55-82,125(1980) discloses the addition of 0.01 to 10% by weight of a water-soluble inhibitor such as ammonium thiocyanate or cupric chloride to water, JP-A-60-8,302(1985) discloses the addition of vanadium pentoxide and/or cupric chloride in combination with a dispersion stabilizer, JP-A-62-205,108(1987) discloses the solution in water of not less than 10 ppm, based on the total amount of vinyl monomers, of such a water-soluble inhibitor as sodium nitrite, potassium nitrite, or cupric chloride, JP-A-2-284,905(1990) discloses suspension polymerization effected by the use of a water-soluble inhibitor such as a nitrite and a polymerization initiator formed of an organic peroxide, and JP-A-3-237,105(1991) discloses suspension polymerization effected in a continuous aqueous phase containing water, a water-miscible organic solvent, and a water-soluble polymerization inhibitor such as sodium nitride or hydroquinone.

Further, as disclosed in JP-A-61-255,353 (1986), the technique of adding to an aqueous suspension polymerization system a water-soluble mercaptan compound for the prevention of the sympathetic occurrence of emulsion polymerization has been known to the art. As water-soluble mercaptan compounds, 2-mercaptoethanol, thioglycolic acid, cysteine, glutathione, dimercaprol, 1,4-dithiothreitol, dimercaptosuccinic acid, and 2,3-dimercapto-1-propanesulfonic acid are cited in the specification in support of the disclosure.

JP-A-52-102,391(1977) discloses the addition of about 0.0005 to about 0.02 part by weight of a water-soluble inhibitor selected from among borohydrides represented by the following structural formula, alkali metal nitrites, alkaline earth metal nitrites, and ammonium nitrite and about 0.0001 to about 0.005 parts by weight of an oil-soluble inhibitor, oil-soluble and alcohol-soluble nigrosine, respectively based on 100 parts by weight of monomer.

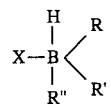

(wherein X is an alkali metal and R, R', and R" independently represent a hydrogen atom, a phenyl group, an alkoxy group, or an alkyl group of one to ten carbon atoms).

JP-A-5-61,253(1993) discloses the suspension polymerization under the presence of a water-soluble nigrosine. Further, JP-A-5-93005(1993) discloses the addition of a metal complex compound of monoazo dye represented by the following formula, in the suspension polymerization method which comprises preserving a continuous phase and a dispersive phase having at least a polymerizable monomer in separate containers, supplying at a controlled ratio these phases through respective passes to a size enlargement apparatus one or more times in order to obtain a suspension which contains polymerizable drops have a desired size, then introducing the suspension to a polymerizing container in order to finish the polymerization of the monomer, and the metal complex compound being added to the continuous phase.

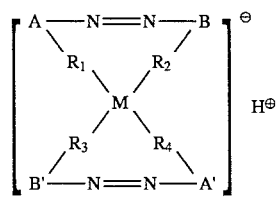

(wherein A, A' are independently a non-substituted or substituted phenylene group, B, B' are independently a non-substituted or substituted naphtyl group, M is a metal atom, $R_1$, $R_2$, $R_3$, $R_4$ are independently O, NH, or O—O.)

In the suspension polymerization of a polymerizable monomer such as a (meth)acryl type monomer, even when an inorganic water-soluble inhibitor is added to the reaction system, the effect of the inhibitor in preventing the emulsion polymerization is so weak that the inhibitor must be added in a large amount. Particularly, the conspicuity of this trend grows in proportion as the diameter of minute particles obtained by the suspension polymerization decreases.

When the water-soluble mercaptan compound mentioned above is used for preventing the sympathetic occurrence of emulsion polymerization, this mercaptan compound induces impartation of an offensive odor to the produced resinous particles or the effluent from the polymerization system. This offensive odor is not easily removed by washing.

As regards the use of the borohydride as a water-soluble inhibitor, this compound itself is difficult to handle and, on account of this difficulty, the conditions of the suspension polymerization dictate rigid control.

When the water-soluble nigrosine compound mentioned above is used, the effect of the compound in preventing the emulsion polymerization is also so weak that the compound must be added in a large amount. To add the compound in a large amount tends to shift the electrical charge property of the obtained particles to positive.

When the metal complex compound of monoazo dye mentioned above is used, some problems in the environmental pollution and the safety is grown up since the heavy metal such as chromium is contained in the polymerization system, and also in the resinous particles obtained.

SUMMARY OF THE INVENTION

An object of this invention, therefore, is to provide a new emulsion polymerization inhibitor and a suspension polymerization method using the inhibitor. Another object of this invention is to provide suspension polymerized resinous particles which only sparingly suffer from the inclusion therein of microfine particles as by-product produced by emulsion polymerization and a method for the production thereof. Yet another object of this invention is to provide a suspension polymerization method which represses the possible yield of the microfine particles as by-product which are produced by the emulsion polymerization being at the phase boundary of the suspended particles and concurring with the suspension polymerization of the polymerizable monomer, and promotes the improvement of stability of polymerization, the enhancing the yield of production, and the enhancement of physical properties of the produced particles.

The objects described above are accomplished by an emulsion polymerization inhibitor which is characterized by containing an aromatic series compound which has at least one $NO_2$ group(s), at least one $SO_3Na$ group(s), and at least one secondary amino group(s).

As the emulsion polymerization inhibitor, the compound represented by the following structural formula (I) is particularly preferable.

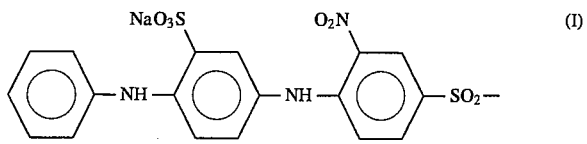

(I)

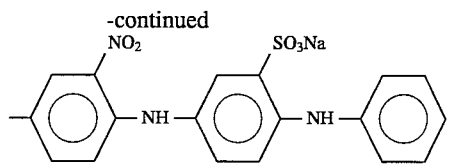

The objects described above are further accomplished by a suspension polymerization method which is characterized by polymerizing a polymerizable monomer suspended in aqueous medium in the presence of the above mentioned aromatic series compound.

In the suspension polymerization method according to the present invention, it is preferable that the polymerizable monomer is a styrene type monomer and/or a (meta)acrylic type monomer.

With respect to the suspension polymerization, it is permitted to incorporate into the polymerization system any additives such as coloring agent, magnetic powder, off-set preventing agent, charge controlling agent, plasticizer, polymerization stabilizer, antistatic agent, and flame retardant.

The objects described above are further accomplished by resinous particles which are obtained by suspension polymerizing the polymerizable monomer in the presence of the aromatic series compound.

The resinous particles may contained any additives as mentioned above in order to suit their use.

As the coloring agent which may be added to the resinous particle, a polymer grafted carbon black is preferable.

Further, this invention is also aimed to an electrophotographic toner using the resinous particle mentioned above.

In this specification the term "emulsion polymerization inhibiter" means an additive agent which has a function of repressing the emulsion polymerization which may occur as a secondary polymerization scheme in the aqueous phase of suspension polymerization system where the aqueous suspension polymerization of the polymerizable monomer should be expected.

We, inventors have made a diligent study in search of a method for repressing the emulsion polymerization as the secondary reaction which concurs with the aqueous suspension polymerization of a polymerizable monomer. As a result, we have acquired a knowledge that when the aromatic series compound which has $NO_2$ group(s), $SO_3Na$ group(s), and secondary amino group(s) each groups being at least one is presented in the suspension polymerization system, the emulsion polymerization which would be found on the phase boundary of the suspended particles can be effectively repressed.

Some of such aromatic series compounds having $NO_2$ group(s), $SO_3Na$ group(s), and secondary amino group(s) have been known as the acid dyes. However, it has never been known and thought by persons skilled in the art that such aromatic series compound has a repressive effect for the emulsion polymerization.

Further, the aromatic series compound is desirable in the standpoints of the environmental pollution and the safety since it has no heavy metal inherently, which differs from the metal complex compound disclosed in JP-A-5-93,005.

Furthermore, when an electrophotographic toner is prepared by using the suspension polymerization method of present invention, it is easy to control the charge property of the toner to desirable one, regardless of the polarity positive or negative, by after-processing the obtained resinous particles with a preferable charge controlling agent which being added outwardly to the particles. it is because that, although the resinous particles obtained by the suspension polymerization in the presence of the aromatic series compound may be contain the aromatic series compound, the amount of the compound contained in the particles is small, therefore, the aromatic series compound used in the suspension polymerization gives substantially no effect to the charge property of the resinous particles obtained.

Thus, this invention can repress the possible secondary occurrence of the emulsion polymerization and promote enhancement of the physical properties, especially heat stability and uniformity of the particle diameters, of the produced particles without the heavy metal contamination.

DETAILED DESCRIPTION OF THE INVENTION

Now, this invention will be described in detail below with reference to embodiments thereof.

The emulsion polymerization inhibitor of the present invention the aromatic series compound which has at least one $NO_2$ group(s), at least one $SO_3Na$ group(s), and at least one secondary amino group(s). Viewing from a different standpoint, the compound is classified as the aromatic ampholytic surfactant having at least one $SO_3Na$ group(s) and at least one secondary amino group(s).

As the emulsion polymerization inhibitor, the compound known as C. I. 10410 (C. I. Acid Brown 13) and represented by the following structural formula (I) is particularly preferable.

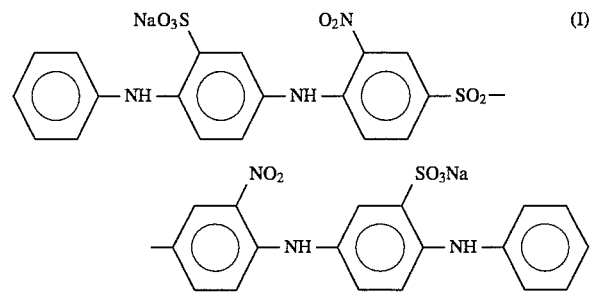

The polymerizable monomer which is usable for the suspension polymerization in the presence of the above mentioned emulsion polymerization inhibitor may any of suspension polymerizable monomers which include, but not limited to, for example, styrene type monomers such as styrene, o-methyl styrene, m-methyl styrene, p-methyl styrene, alpha-methyl styrene, p-methoxy styrene, p-tertbutyl styrene, p-phenyl styrene, o-chlorostyrene, m-chlorostyrene, and p-chlorostyrene; acryl or methacryl type monomers such as methyl acrylate, ethyl acrylate, n-butyl acrylate, isobutyl acrylate, dodecyl acrylate, stearyl acrylate, 2-ethylhexyl acrylate, methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, acrylic acid and metacrylic acid; and ethylene, propylene, butylene, vinyl chloride, vinyl acetate, and acrylonitrile. These polymerizable monomers may be used either singly or in the form of a mixture of two or more members. Particularly, a styrene type monomer, an acryl or methacryl type monomer or a combination thereof is desirable.

For the purpose of obtaining resinous particles having an intermolecular cross-linked structure, it is allowable to copolymerize a (meth)acryl type monomer having a plurality of polymeric double bond groups in the molecular unit thereof with the aforementioned (meth)acryl type monomer. The cross-linking (meth)acryl type monomers which answer the description given above include, for example, trimethylol propane triacrylate, ethylene glycol dimethacrylate, diethylene glycol dimethacrylate, triethylene glycol dimethacrylate, decaethylene glycol dimethacrylate, pentadecaethylene glycol dimethacrylate, pentacontahectaethylene glycol dimethacrylate, 1,3-butylene dimethacrylate, allyl methacrylate, trimethylol propane trimethacrylate, pentaerythritol tetramethacrylate, and diethylene glycol dimethacrylate. It is allowable to use a plurality of these (meth)acryl type monomers in a combined state. It is permissible to use in the copolymerization as a cross-linking agent an aromatic divinyl compound such as divinyl benzene, divinyl naphthalene, or a derivative thereof, a cross-linking agent such as N,N-divinyl aniline, divinyl ether, divinyl sulfide, or divinyl sulfonic acid, an unsaturated polyester such as polybutadiene or polyisoprene, and any of the reactive polymers disclosed in JP-B-57-56,507, JP-A-59-221,304, JP-A-59-221,305, JP-A-59-221,306, and JP-A-59,221,307.

The suspension polymerization method of the present invention, in the aqueous suspension polymerization of the polymerizable monomer above mentioned, requires the addition of the above mentioned aromatic series compound which has at least one $NO_2$ group(s), at least one $SO_3Na$ group(s), and at least one secondary amino group(s) to the suspension polymerization system.

In the aqueous suspension polymerization contemplated by this invention, although the amount of the aromatic series compound to be added is affected as by, for example, the type of the compound used and the composition of the polymerizable monomer, it is in the range of 0.0001 to 10% by weight. If the amount of the aromatic series compound to be added is less than 0.0001% by weight, the effect of this compound in inhibiting emulsion polymerization is too small to prevent the occurrence of microfine particles. Conversely, even if the addition amount of the compound exceeds 10% by weight, the inhibition effect for emulsion suspension is substantially equal to that obtained by the amount of 10% by weight, and is saturated, thus the addition amount of more than 10% by weight would be not desirable from the economical view. In an embodiment of the present invention where the obtained resinous particles are used for the electrophotographic toner, the amount of 0.001 to 3% by weight, particularly 0.01 to 1% by weight is desirable, since a problem in the environmental stability of the product would come out as the addition amount of the aromatic series compound is increased.

The method for adding this aromatic series compound to the suspension polymerization system is not particularly specified. For example, a method which comprises adding the compound into the polymerizable monomer, a method which comprises adding the compound to the aqueous phase, and the method which comprises dissolving the compound in a solvent such as methanol and dispersing the resultant solution in the aqueous phase, are available.

The method of this invention for the production of resinous particles resides in subjecting the polymerizable monomer as described above to aqueous suspension polymerization in the presence of the aromatic series compound as described above. The polymerization temperature suitably is in the approximate range of 10° to 90° C., preferably 30° to 80° C. This suspension polymerization is preferably carried out either after regulation of diameter of the suspended particles of polymerizable monomer has been completed or while the regulation is in process. Preferably, it is carried out after regulation of the particle diameter. This regulation of the particle diameter is effected by dispersing the prescribed reactant components in an aqueous medium and stirring the resultant suspension using a T.K. Homomixer. It may otherwise be effected by passing the reactant components once to several times through a high-speed stirring device such as a line mixer (Ebara Milder of Ebara Mgf. Co. Ltd., Japan, for example).

The suspension polymerization system may incorporate therein a dispersion stabilizer with a view to stabilizing the suspended particles. The dispersion stabilizers which are effectively used herein include, but not limited to, for example, water-soluble macromolecular compounds such as polyvinyl alcohol, gelatin, tragacanth, starch, methyl cellulose, carboxy methyl cellulose, hydroxy ethyl cellulose, sodium polyacrylate, and sodium polymethacrylate, anionic surfactants, cationic surfactants, ampholytic surfactants, nonionic surfactants, and alginates, zein, casein, barium sulfate, calcium sulfate, barium carbonate, magnesium carbonate, calcium phosphate, talc, clay, diatomaceous earth, bentonite, titanium hydroxide, thorium hydroxide, and powdered metal oxides.

As the anionic surfactants, fatty oils such as, for example, sodium oleate and potassium salt of castor oil, alkyl sulfates such as sodium lauryl sulfate and ammonium lauryl sulfate, alkyl benzene sulfonates such as dodecyl benzene sulfonate, alkyl naphthalene sulfonates, alkane sulfonates, dialkylsulfosuccinates, alkyl phosphoric esters, condensates of naphtalene sulfonic acid with formalin, polyoxyethylene alkylphenylether sulfates, and polyoxyethylene alkyl sulfates are cited. The nonionic surfactant includes polyoxyethylene alkyl ethers, polyoxyethylene alkylphenyl ethers, polyoxyethylene fatty esters, sorbitan fatty esters, polyoxysorbitan fatty esters, polyoxyethylene alkylamines, glycerol fatty esters, oxyethylene—oxypropylene block polymers. The cationic surfactant includes, for example, alkylamine salts such as lauryl amine acetate and stearyl amine acetetes, and quaternary ammonium salts such as lauryl trimethylammonium chloride, for example. The ampholytic surfactant includes lauryl dimetyl amine oxide.

The dispersion stabilizer must be used with the composition thereof and the amount of use thereof suitably adjusted so that the produced resinous particles will acquire a prescribed diameter in the range of 0.1 to 500 μm, preferably 0.5 to 100 μm, and more preferably 0.5 to 30 μm. Specifically, the amount of the dispersion stabilizer used is in the range of 0.01 to 29% by weight, preferably 0.1 to 10% by weight, based on the amount of the polymerizable monomer.

As the polymerization initiator to be used for the polymerization in this invention, any of the oil-soluble peroxide type and azo type initiators which are generally used for suspension polymerization can be adopted. The initiators which are effectively used herein include, for example, peroxide type initiators such as benzoyl peroxide, lauroyl peroxide, octanoyl peroxide, benzoyl orthochloroperoxide, benzoyl orthomethoxyperoxide, methylethyl ketone peroxide, diisopropyl peroxy dicarbonate, cumene hydroperoxide, cyclohexanone peroxide, t-butyl hydroperoxide, and diisopropyl benzene hydro-peroxide, and azo type initiators such as 2,2'-azo-bis-isobutyronitrile, 2,2'-azo-bis(2,4-dimethyl valeronitrile), 2,2'-azo-bis-(2,3-dimethyl butyronitrile), 2,2'-azo-bis(2-dimethyl butyronitrile), 2,2'-azo-bis(2,3,3-trimethyl butyronitrile), 2,2'-azo-bis(2-isopropyl butyronitrile), 1,1'-azo-bis(cyclohexane-1-carbonitrile), 2,2'-azo-bis(4-methoxy-2,4-dimethyl valeronitrile), 2-(carbamoyl-azo) isobutyronitrile, 4,4'-azo-bis(4-cyanovaleric acid), and dimethyl-2,2'-azo-bis-isobutyrate. The polymerization initiator is preferably used in an amount in the range of 0.01 to 20% by weight, more preferably 0.1 to 10% by weight, based on the amount of the polymerizable monomer.

In preparation for the suspension polymerization, the polymerizable monomer or the aqueous phase, when necessary, may have a coloring agent such as a pigment or dye or other additive such as a magnetic powder, an off-set preventing agent, a charge controlling agent, a plasticizer, a polymerization stabilizer, an antistatic agent, and a flame retardant incorporated therein or added thereto.

The pigments which are usable effectively used herein include, but not limited to, for example, inorganic pigments such as white lead, minium, chrome yellow, carbon black, ultramarine, zinc oxide, cobalt oxide, titanium dioxide, iron oxide, silica, titanium yellow, and titanium black; and yellow pigments such as navel yellow, naphthol yellow S, Hansa yellow 10G, benzidine yellow G, benzidine yellow GR, quinoline yellow lake, permanent yellow NCG, and tartrazine lake; orange pigments such as molybdenum orange, permanent orange RK, benzidine orange G, and indanthrene brilliant orange GK; red pigments such as permanent red 4R, resor red, pyrazolone, red 4R, watching red calcium salt, lake red D, brilliant carmine 6B, eosin lake, rhodamine lake B, azaline lake, and brilliant carmine B; purple pigments such as fast violet B and methyl violet lake; blue pigments such as alkali blue lake, victoria blue lake, phthalocyanine blue, nonmetallic phthalocyanine blue, partial chloride of phthalocyanine blue, fast sky blue, and indans blue BC; green pigments such as pigment green B, malachite green lake, and fanal yellow green G; and other organic pigments such as isoindolinone, quinacridone, perinone pigment, insoluble azo pigments, soluble azo pigments, and color lake.

The dyes which are effectively used herein include, but not limited to, for example, nitroso dye, nitro dye, azo dye, stilbene azo dye, diphenyl methane dye, triphenyl methane dye, xanthene dye, acridine dye, quinoline dye, methine dye, polymethine dye, thiazole dye, indamine dye, indophenol dye, azine dye, oxazine dye, thiazine dye, and sulfide dye.

The magnetic powder which are effectively used herein include, but not limited to powders of ferromagnetic metals such as iron, cobalt, and nickel and powders of metallic compounds such as magnetite, hematite, and ferrite, for example. The magnetic powder may be colored and can be used as coloring agent either independently or in combination with other coloring agent.

The coloring agent and other additive mentioned above may have been given a surface treatment by various method for the purpose of having the dispersibility thereof in the polymerizable monomer improved. The methods which are effectively used for the surface treatment include, for example, a method which effects the treatment with a long-chain hydrocarbon such as stearic acid or oleic acid, a method which effects the treatment with a polymerizable monomer having a polar group such as an acrylic acid or a methacrylic acid, a method which effects the treatment with a polyhydric alcohol such as a trimethylol propane, a method which effects the treatment with an amine such as triethanol amine, a method which effects the treatment with various coupling agent, and a method which comprises causing the coloring agent or other additive to react at a temperature in the range of 20° to 350° C. with a polymer having a reactive group such as aziridine group, oxazoline group, N-hydroxyalkylamide group, epoxy group, thioepoxy group, isocyanate group, vinyl group, silicon type hydrolyzing group, or amino group which can react with the functional group on the surface of the coloring agent or other additive mentioned above thereby grafting the polymer on the surface of the coloring agent or other additive. When carbon black is used as the coloring agent, for example, the carbon black graft polymer disclosed in JP-A-63-270,767(1988) and JP-A-63-265,913(1988) (U.S. Pat. No. 4,880,857, U.S. Pat. No. 4,940,749, and U.S. Pat. No. 4,994,520) proves to be ideal. When a coloring agent other than carbon black is used, the surface-treated coloring agent produced by the method disclosed in JP-A-1-118,573(1989) proves to be ideal. These are associated herein by reference.

In the embodiment what is prepared by the suspension polymerization method of the present invention is the electrophotographic toner, to add the off-set preventing agent as well as the coloring agent and/or magnetic powder is desirable. The off-set preventing agent which are effectively used herein include, but not limited to, polymers having a ring softening point in the range of from 80° C. to 180° C., for example polyolefins having a weight average molecular weight (Mw) in the range of 1,000 to 45,000, particularly, 2,000 to 6,000, which are called as polyolefin waxes. The polyolefin waxes include, for example, homopolymers such as polyethylene, polypropylene, and polybutylene; olefins copolymer such as etylenepropylene copolymer, ethylene-butene copolymer, etylenepentene copolymer, ethylene-3-methyl-1-butene copolymer, ethylene-propylene-butene-terpolymer; and copolymer of olefin and other monomers including, for example, vinyl ethers such as vinylmethyl ether, vinyl-n-butyl ether, and vinylphenyl ether; vinyl esters such as vinylacetate, vinylbutylate; haloolefins such as vinyl fluoride, vinylidene fluoride, tetrafluoroethylene, vinyl chloride, vinylidene chloride, and tetrachloroethylene; (meth-)acryl esters such as methyl acrylate, ethyl acrylate, n-butyl acrylate, methyl methacrylate, ethyl methacrylate, n-butyl methacrylate, stearyl methacrylate, N,N-dimethylaminoetyl metacrylate, and t-butylaminoethyl methacrylate; acrylic acid derivatives such as acrylonitrile and N,N-dimethylacrylamide; organic acids such as acrylic acid, methacrylic acid, maleic acid, fumaric acid, itaconic acid; and diethyl fumarate, β-pinene and etc.

Further, some compounds other than the above polyolefins may be used as the off-set preventing agent, which include natural or synthetic paraffin waxes, particularly, high-melting paraffin waxes having a melting point in the range of 70° C. to 60° C.; metal salts of fatty acid such as zinc, barium, lead, cobalt, calcium or magnesium stearate, zinc, manganese, iron or lead oleate, and cobalt, zinc, cobalt, or magnesium palmitate, particularly, salts of higher fatty acids having more than 17 of carbon atoms; higher alcohols such as myricyl alcohol; esters of polyhydroxy alcohols such as stearin and palmitin; fatty esters such as myricyl stearate, myricyl palmitate; partial saponified fatty esters such as partial saponified montanate; higher fatty acids such as stearic acid, palmitic acid and montanic acid; fatty amides such as etylene-bis(stearoyl) amide; and mixtures thereof.

The charge controlling agents which may be used optionally when the electrophotographic toner is prepared include, but not limited to, nigrosine, monoazo dyes, zinc hexadecyl succinate, alkyl esters or alkyl amines of naphthoic acid, nitrofunic acid, N-N'-tetramethyldiamine benzophenone, triazine and metal complexes of salicylic acid.

In a further preferable embodiment of the present invention, one of agent comprising microfine water-insoluble particles as disclosed in JP-A-5-40,366(1993), and known flocculants is added to the suspension of resinous particles obtained by the suspension polymerization, thereby promoting flocculation of the resinous particles and facilitating the withdrawal of the resinous particles from the suspension medium.

When microfine water-insoluble particles are added to the suspension solution of the resinous particles, the same stable flocculation is effected to form the flocculates having a desirable size as when the known flocculating agent is used, the operation of filtration can be stably performed, and the filtrated resinous particles are free from the drawbacks observed in the product obtained when a known flocculating agent is used.

The microfine water-insoluble particles to be used in the present invention are intended to keep the flocculation of the resinous particles in the optimum condition, enable the resinous particles resulting from the filtration to manifest high physical properties. The particle diameter of the microfine water-insoluble particles, therefore, must be smaller than that of the resinous particles. To be specific, it is desired to be less than one half of the particle diameter of the resinous particles.

As the microfine water-insoluble particles which are used as one kind of flocculating agent in the present invention, various kinds of organic powders and inorganic powders can be used.

The organic powders which are effectively usable herein include cross-linked and non-cross-linked polymer powders, or aforementioned organic pigments, charge controlling agents, and waxes, for example. The cross-linked and non-cross-linked resin powders include styrene type resin powders, acrylic type resin powders, methacrylic type resin powders, polyethylene type resin powders, polypropylene type resin powders, silicone type resin powders, polyester type resin powders, polyurethane type resin powders, polyamide type resin powders, epoxy type resin powders, polyvinyl butyral type resin powders, rosin type resin powders, terpene type resin powders, phenol type resin powders, melamine type resin powders, and guanamine type resin powders, for example.

The inorganic powders which are effectively usable herein include microfine particles or granules of alumina, titanium dioxide, barium titanate, magnesium titanate, calcium titanate, strontium titanate, zinc oxide, silica sand, clay, mica, tabular spar, diatomaceous earth, various inorganic oxide pigments, chromium oxide, cerium oxide, iron red, antimony trioxide, magnesium oxide, zirconium oxide, barium sulfate, barium carbonate, calcium carbonate, silica, silicon carbide, silicon nitride, boron carbide, tungsten carbide, titanium carbide, and carbon black, for example.

Of the water-insoluble powders cited above, those which have a hydrophobicity index ($M_{wet}$: methanol wettability) of at least 5 prove to be particularly desirable because of their ability to impart ideal moistureproofness to the resinous particles to be obtained in consequence of disintegration. They are also beneficial in terms of the stability of charging which is manifested when the resinous particles are used as an electrophotographic toner.

The water-insoluble powders which are particularly desirable as described above include various inorganic oxides such as silica, titanium, and zirconia which have undergone a treatment for impartation of hydrophobicity and electro-conductive species of carbon black such as Ketjen black, acetylene black, and furnace black, for example.

The term "hydrophobicity index" as used herein refers to the numerical value which is obtained by the following procedure.

(1) In a beaker having an inner volume of 200 ml, 0.2 g of a given sample is placed and diluted with 50 ml of purified water.

(2) The aqueous solution of the sample is kept stirred with a magnetic stirrer and methanol is added to the stirred solution under the surface.

(3) The point at which the visible sign of the sample ceases to exist on the surface of the stirred solution is taken as the end point of the test.

(4) The degree of hydrophobicity of the sample is calculated in accordance with the following formula using the amount of methanol consumed in the test.

Hydrophobicity index $(\%)=\{x/(50+x)\}\times 100$ wherein x stands for the amount of methanol used (ml).

In consideration of the charging stability of the toner of a small particle diameter necessary for realizing the production of images of high resolution, the microfine water-insoluble particles to be selected for use herein are desired to possess electroconductivity. The microfine electroconductive water-insoluble particles which are effectively usable herein include powders of electroconductive carbon black, titanium oxide and tin oxide doped with antimony oxide, electroconductive zinc oxide, and titanium black, for example.

To be used effectively for the purpose just mentioned, the microfine water-insoluble particles are desired to have particle diameters in the range of from 0.001 to 10 μm, preferably from 0.005 to 5 μm. If the microfine water-insoluble particles have particle diameters not exceeding 0.001 μm, there arises the possibility that the effect of the addition of these particles, i.e. the notable improvement in the property of flocculation, and the flowability, cleanability, etc. to be manifested by the particles when they are used as an electrophotographic toner, will be no longer manifested. Conversely, if the microfine water-insoluble particles have particle diameters exceeding 10 μm, there ensues the possibility that the effect of the addition of these particles will be unduly low and the improvement in resolution of images to be attained when the particles are used as an electrophotographic toner will not be manifested. The amount of these microfine water-insoluble particles to be added may be selected in a wide range, depending on the kind and particle diameter of the microfine water-insoluble particles to be used. If this amount is unduly small, the effect of the addition of these particles is manifested only with difficulty. If the amount is unduly large, the possibility arises that the particles, when used as an electrophotographic toner, will exert adverse effects on charging property and environmental stability. The amount of addition, therefore, is desired to be in the range of from 0.01 to 100 parts by weight, preferably from 0.1 to 50 parts by weight, based on 100 parts by weight of the polymerizable monomer. The various species of microfine water-insoluble particles cited above may be used either singly or jointly in the form of a mixture of two or more members.

The treatment for flocculation of the resinous particles is performed by adding the microfine water-insoluble particles of the kind described above to an aqueous suspension solution and allowing the resultant mixture to stand for a prescribed period optionally in a stirred state without specifically requiring application of heat. Considering the operations efficiency, however, a heat treatment to a temperature exceeding the Tg of the polymer forming said microfine globular particles may be permissible unless the heat treatment causes excessive fusion of the microfine globular particles.

It goes without saying that even when the microfine water-insoluble particles are used, the known flocculating agent or the bad solvent for microfine globular colored particles which is mentioned above may be simultaneously used unless the combined use brings about an inconvenience. Optionally, a proper organic solvent may be additionally used for the purpose of promoting the fusion.

Alternatively, a non-solvent for the resin of resinous particles can be added to the suspension. The non-solvent for the resin of resinous particles can be induce the flocculation of the resinous particles in the suspension solution in advance of the isolation or fractionation of the resinous particles. Further, to use the non-solvent in combination with the aforementioned microfine water-insoluble particles is desirable since the non-solvent facilitates that the microfine water-insoluble particles reach the surfaces of the individual resinous particles. The non-solvents which are effectively usable for this purpose include, but not limited to, hydrocarbons such as hexane, heptane, octane, and petroleum ether and lower alcohols such as methanol and ethanol, for example. The expression "non-solvent for the resinous particles" as used herein means a solvent which is incapable of dissolving or dispersing the resin forming the resinous particles.

The state of flocculation to be produced by such flocculant or flocculating agent is desired to be such that the flocculates of the resinous particles have a bulk density in the range of from 0.1 to 0.9 g/cm$^3$, preferably from 0.2 to 0.7 g/cm$^3$. Though the flocculates are not limited in shape or size, they are desired to have an average size in the range of from 20 to 10,000 μm, preferably from 30 to 1,000 μm, in consideration of the conveniences of the following operations of filtration, drying, and disintegration. If the size is less than 20 μm, the withdrawal of particles entails consumption of a very large volume of energy or necessitates use of a special device. If this size exceeds 10,000 μm, the disintegration calls for a huge energy.

The solid-liquid separation of the resinous particles and suspension liquid after the flocculation treatment can be easily carried out by using one of known solid-liquid separators in general techniques such as suction filtration, filtration under pressure, or centrifugal filtration.

The agglomerates of particles separated from the suspension liquid are then forwarded to the step of disintegration via the step of drying in order to disintegrate the agglomerates to individual separate particles having substantially same size of before flocculated. By using a disintegrator having a relatively simple mechanism and small energy, the disintegration can be easily attained since resinous particles in the agglomerates adhere each other only at a point or small area.

The resinous particles which are obtained by the method of production of this invention performed as described above avoid by-production of microfine particles due to emulsion polymerization as secondary reaction and have an extremely narrow particle diameter distribution having an average diameter in the approximate range of 0.1 to 500 μm, preferably 0.5 to 100 μm, and more preferably 0.5 to 30 μm because the emulsion polymerization which occurs secondarily at the phase boundary of the suspended particles and the aqueous phase during the suspension polymerization is repressed by the action of the aforementioned aromatic series compound having NO2 group(s), SO$_3$Na group(s), NO2 group(s) and secondary amino group(s).

Since the resinous particles obtained by the method of production of this invention or the liquid having such resinous particles suspended therein can be ideally used in various applications because the resinous particles have outstanding properties such as a very narrow particle diameter distribution as described above, and no heavy metal content.

For example, the resinous particles obtained by this invention on condition that the coloring agent is added to the polymerizable monomer are ideally used as a electrophotographic toner.

The electrophotographic toner according with the present invention uses the colored resinous particles mentioned above. In order for this toner to possess a proper charging property, the average particle diameter is ideally in the range of from 3.5 to 20 μm, preferably from 4 to 15 μm.

The colored resinous particles may be used in their unmodified forms as an electrophotographic toner.

Alternatively, such additives as a charge controlling agent for the adjustment of charging and a fluidifying agent which are normally used in ordinary toners may be properly incorporated in the microfine colored particles of the present invention.

The method for effecting the incorporation of a charge controlling agent is not particularly restricted. Any of the known methods available for the purpose of this incorporation may be adopted. For example, a method which comprises having the charge controlling agent incorporated in the polymeric monomer in advance of the polymerization of the polymeric monomer having a coloring agent dispersed therein, and a method which comprises causing the charge controlling agent to be deposited fast on the surface of the resinous colored particles by aftertreating the microfine colored particles with the charge controlling agent may be properly adopted. particularly, by using the latter method, and thus adding the charge controlling agent outwardly to the surface of the resinous colored particles, the charge property of the toner is easy control to desirable one, regardless of the polarity positive or negative.

Besides the uses mentioned above, the resinous particles of this invention can be ideally used, for example, as a coloring agent for thermoplastic plastics or a thermosetting plastics, an additive for coating composition, an additive for artificial marble, or an additive for a facing panel in the embodiment of containing coloring agent; and a filler for a chromatographic column, a gap-adjusting agent for a liquid crystal display panel, a display powder for a Coulter Counter, and a carrier for an immunodiagnostic medicine in the embodiments of containing and not containing coloring agent.

EXAMPLES

Now, this invention will be described more specifically below with reference to the working examples. These examples will not limit this invention in any respect. Wherever the expression "parts" is used in the following working examples, it shall be construed invariably as referring to parts by weight.

Example 1

A flask provided with a stirrer, an inert gas inlet tube, a reflux condenser, and a thermometer was charged with 900 parts of deionized water having dissolved therein 0.5 part of polyoxy-ethylene alkylsulfo-ammonium (produced by Dai-ichi Kogyo Seiyaku Co., Ltd., (Japan) and marketed under trademark designation of "Hitenol N-08"). To the flask, as the emulsion polymerization inhibitor, 0.01 part of C. I. 10410 (produced by Nippon Kayaku Co., Ltd., (Japan) and marketed under trademark designation of "4GW") was added, then a mixture prepared in advance of 80 parts of styrene, 20 parts of n-butyl acrylate and 0.5 part of azoisobutyronitrile was added. The resultant mixture was stirred for five minutes at a rate of 8000 r.p.m. with a T. K. Homogenizer (a proprietary product of Tokushu Kika Kogyo K.K.) to give rise to a homogeneous suspension.

Then, the suspension was blown with a forced current of nitrogen gas and, at the same time, heated to 75° C. Then, it was continuously stirred at this temperature for five hours to effect suspension polymerization and thereafter cooled. The suspension was filtered and then dried to obtain resinous particles (1).

The produced resinous particles (1) were tested for properties and the amount of microfine particles by-produced by emulsion polymerization was determined. The results are shown in Table 1.

Example 2

To the same apparatus of Example 1, 900 parts of deionized water having dissolved therein 0.5 part of polyoxyethylene alkylsulfo-ammonium (produced by Dai-ichi Kogyo Seiyaku Co., Ltd., (Japan) and marketed under trademark designation of "Hitenol N-08") was added, and then, 0.5 part of C. I. 10410 (produced by Nippon Kayaku Co., Ltd., (Japan) and marketed under trademark designation of "4GW") was added as the emulsion polimerization inhibitor. Then a mixture prepared in advance of 95 parts of methyl methacrylate, 15 parts of methyl acrylate and 1 part of 2,2'-azo-bis-(2,4-dimetylvaleronitrile) (Nippon Hydrazine Co., Ltd., (Japan) and marketed under trademark designation of "V-65") was added. Thereafter, along the same procedure as shown in Example 1, resinous particles (2) were obtained.

The produced resinous particles (2) were tested for properties and the amount of microfine particles by-produced by emulsion polymerization was determined in the same manner as in Example 1. The results are shown in Table 1.

Synthetic Example 1

In a flask provided with a stirrer, an inert gas inlet tube, a reflux cooling tube, and a thermometer, 2,000 parts of deionized water having 1 part of polyvinyl alcohol dissolved therein was placed. In this water, a mixture prepared in advance by dissolving 8 parts of benzoyl peroxide in a polymeric monomer consisting of 97 parts of styrene, 3 parts of glycidyl methacrylate was stirred at a high speed to form a homogeneous suspension. Then, the suspension was exposed to the blow of nitrogen gas and, at the same time, heated to 80° C., stirred continuously at this temperature for five hours to undergo polymerization, and then deprived of water, to obtain a polymer having an epoxy group as a reactive group.

By the use of a laboratory plastomill (produced by Toyo Seiki K.K.), 40 parts of the polymer having an epoxy group as a reactive group and 20 parts of carbon black (produced by Mitsubishi Chemical Industries, Ltd. and marketed under product code of "MA-100R") were kneaded to effect reaction under the conditions of 160° C. and 100 r.p.m., then cooled and pulverized to obtain a carbon black graft polymer (1).

Example 3

To the same apparatus of Example 1, 900 parts of deionized water having dissolved therein 0.5 part of polyoxyethylene alkylsulfo-ammonium (produced by Dai-ichi Kogyo Seiyaku Co., Ltd., (Japan) and marketed under trademark designation of "Hitenol N-08") was added, and then, 0.05 part of C. I. 10410 (produced by Nippon Kayaku Co., Ltd., (Japan) and marketed under trademark designation of "4GW") was added as the emulsion polimerization inhibitor. Then a mixture prepared in advance of 30 parts of carbon black graft polymer (1) obtained by Synthetic Example 1 mentioned, 85 parts of styrene, 15 parts of n-butyl acrylate, 0.3 part of divinyl benzene, 2 parts of azo-bis-isobutylonitril and 4 part of 2,2'-azo-bis-(2,4-dimetylvaleronitrile) (Nippon Hydrazine Co., Ltd., (Japan) and marketed under trademark designation of "V-65") was added. Thereafter, along the same procedure as shown in Example 1, colored resinous particles (3) were obtained.

The produced colored resinous particles (3) were tested for properties and the amount of microfine particles by-produced by emulsion polymerization was determined in the same manner as in Example 1. The results are shown in Table 1.

Control 1

Along the same procedure of Example 1, except the addition of C. I. 10410 (produced by Nippon Kayaku Co., Ltd., (Japan) and marketed under trademark designation of "4GW") was omitted, the process of suspension polymerization was repeated. However, the greater part of the suspended drops agglomerated during the process of suspension polymerization and it resulted in failure. The desired resinous particles were not obtained.

Control 2

Along the same procedure of Example 1, except 1 part of cupric chloride was added instead of C. I. 10410 (produced by Nippon Kayaku Co., Ltd., (Japan) and marketed under trademark designation of "4GW"), the process of suspension polymerization was repeated. However, the greater part of the suspended drops agglomerated during the process of suspension polymerization and it resulted in failure. The desired resinous particles were not obtained.

Control 3

Along the same procedure of Example 1, except 1 part of thioglycolic acid was added instead of C. I. 10410 (produced by Nippon Kayaku Co., Ltd., (Japan) and marketed under trademark designation of "4GW"), the process of suspension polymerization was repeated in order to obtain colored resinous particles (C3) for comparison.

The produced resinous particles (C3) for comparison were tested for properties and the amount of minute particles by-produced by emulsion polymerization was determined in the same manner as in Example 1. The results are shown in Table 1.

Examples 4–5 and Referential Examples 1–2

Along the procedure of Example 1, except the amount of C. I. 10410 (produced by Nippon Kayaku Co., Ltd., (Japan) and marketed under trademark designation of "4GW") was changed to 0.00005 part (Referential Example 1), 0.0001 part (Example 4), 10 parts (Example 5), or 15 parts (Referential Example 2), respectively, resinous particles were obtained in each Examples.

The each resinous particles obtained were tested for properties and the amount of minute particles by-produced by emulsion polymerization was determined in the same manner as in Example 1. The results are shown in Table 1.

Example 6

90 parts of carbon black graft polymer (1) obtained by Synthetic Example 1 mentioned, 10 parts of low molecular polypropylene (produced by Sanyo Chemical Industries Co., Ltd. (Japan) and marketed under trademark designation of "Viscol 660P"), 1 part of graft modified wax (produced by Mistui Petroleum and Chemical Industries Co., Ltd. (Japan) and marketed under trademark designation of "Mitsui Hi-Wax HW1160H"), and 3 parts of charge controlling agent (produced by Hodogaya Kagaku Kogyo K.K. (Japan) and marketed under trademark designation of "Aizen Spilon Black TRH") were blended and mixed by Super Mixer (manufactured by K.K. Kawata(Japan)) under the conditions of 1,000 rpm for 3 minutes. Then, the resultant mixture was kneaded by a twin-screw extruder (manufactured by Ikegai K.K. (Japan) and marketed under trademark designation of "PCM-45-30") under the conditions of 60 rpm at 135° C. for 5 minutes in order to obtain a wax and charge controlling agent contained carbon black graft polymer (1). After cooling, the carbon black graft polymer (1) was granulated by a cutter mill (manufactured by Nishimura Kikai K.K. (Japan)) to obtain granular wax and charge controlling agent contained carbon black graft polymer (1').

To 85 parts of styrene and 15 parts of butyl acrylate, 50 parts of the granular wax and charge controlling agent contained carbon black graft polymer (1'), 2 parts of azo-bis-isobutylonitril and 4 part of 2,2'-azo-bis-(2,4-dimetylvaleronitrile) was dissolved. Then, the resultant mixture was added to 700 parts of deionized water having dissolved therein 1 part of sodium dodecylbenzene sulfonate and 1 part of C. I. 10410 (produced by Nippon Kayaku Co., Ltd., (Japan) and marketed under trademark designation of "4GW"). The resultant mixture was stirred for five minutes at a rate of 7,000 r.p.m. with a T. K. Homogenizer (a proprietary product of Tokushu Kika Kogyo K.K.) to give rise to a homogeneous suspension.

Then, the suspension was blown with a forced current of nitrogen gas and, at the same time, heated to 65° C. Then, it was continuously stirred at this temperature for three hours and then at 75° C. for another 5 minutes to effect suspension polymerization and thereafter cooled. The suspension was filtered and then dried to obtain colored resinous particles (6).

The produced colored resinous particles (6) were used in their unmodified forms as an electrophotographic toner (6). To 5 parts of the toner (6), 95 parts of an carrier of iron powder having a mean particle diameter of 50 to 80 μm was mixed homogeneously to obtain a developing agent (6). The prepared developing agent (6) were determined for the charge amounts under the conditions of 60% RH at 23° C. , and 90% RH at 30° C. The results are shown in Table 2.

Examples 7–8

Along the procedure of Example 6, except the amount of C. I. 10410 (produced by Nippon Kayaku Co., Ltd., (Japan) and marketed under trademark designation of "4GW") was changed to 3.0 part (Example 7), or 5.0 part (Example 8) respectively, colored resinous particles were obtained in each Examples.

The produced colored resinous particles were tested for properties and determined for the amounts of minute particles by-produced by emulsion polymerization in the same manner as in Example 1. The results are shown in Table 1.

Further, the charged amounts were determined in the same manner as in Example 6, when the each produced colored resinous particles were used in their unmodified forms as electrophotographic toners. The results are shown in Table 2.

TABLE 1

| No. | Resinous particles | Amount of the emulsion suspension inhibitor (parts) | Particle diameter (μm) | distribution of particle diameters (μm) | Amount of the emulsion polymerized particle |
|---|---|---|---|---|---|
| Control 1 | | 0 | greater parts agglomerated during the suspension polymerization | | |
| Ref. Ex. 1 | | 0.00005 | greater parts agglomerated during the suspension polymerization | | |
| Example 4 | (4) | 0.0001 | 4.07 | 2.91 | 2.09 |
| Example 1 | (1) | 0.01 | 4.00 | 1.81 | 0.27 |
| Example 2 | (2) | 0.03 | 3.86 | 1.37 | 0.29 |
| Example 3 | (3) | 0.05 | 4.38 | 1.70 | 0.33 |
| Example 6 | (6) | 1.0 | 3.98 | 1.50 | 0.13 |
| Example 7 | (7) | 3.0 | 4.30 | 1.48 | 0.05 |
| Example 8 | (8) | 5.0 | 4.28 | 1.46 | 0.01 |
| Example 5 | (5) | 10.0 | 3.80 | 1.43 | N.D. |
| Ref. Ex. 2 | (R2) | 15.0 | 3.78 | 1.44 | N.D. |
| Control 2 | | 1 cupric chloride | greater parts agglomerated during the suspension polymerization | | |
| Control 3 | (C3) | 1 thioglycolic acid | 4.10 | 2.00 | 1.80 |

N.D.: Not determined

TABLE 2

| No. | Charge amounts (μC/g) under 23° C., 60% RH | Charge amounts (μC/g) under 30° C., 90% RH |
|---|---|---|
| Example 6 | −20 | −17 |
| Example 7 | −20 | −16 |
| Example 8 | −19 | −10 |

What is claimed is:

1. A suspension polymerization method comprising polymerizing a polymerizable monomer suspended in aqueous medium in the presence of an emulsion polymerization inhibitor comprising an aromatic series compound which has a $NO_2$ group, a $SO_3Na$ group, and a secondary amino group represented by the following structural formula (I)

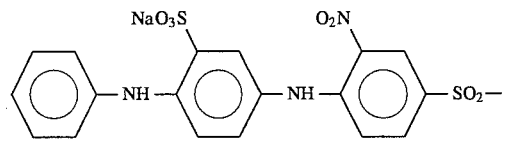

(I)

-continued

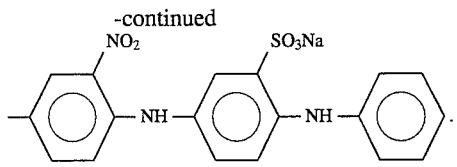

2. A suspension polymerization method according to claim 1, wherein the amount of said aromatic series compound to be added is in the range of 0.0001 to 10 parts by weight per 100 parts by weight of said polymerizable monomer.

3. A suspension polymerization method according to claim 1, wherein said polymerizable monomer is one of styrene type monomers and (meta)acrylic type monomers.

4. A suspension polymerization method according to claim 1, the system ready for suspension polymerization has incorporated therein an additive selected from the group consisting of coloring agent, magnetic powder, charge controlling agent, off-set preventing agent, polymerization stabilizer, antistatic agent, and flame retardant.

* * * * *